United States Patent [19]
Frost

[11] Patent Number: 5,929,080
[45] Date of Patent: Jul. 27, 1999

[54] METHOD OF TREATING POLYCYSTIC KIDNEY DISEASE

[75] Inventor: Philip Frost, Morris Township, N.J.

[73] Assignee: American Cyanamid Company, Madison, N.J.

[21] Appl. No.: 09/063,452

[22] Filed: Apr. 21, 1998

Related U.S. Application Data

[60] Provisional application No. 60/045,679, May 6, 1997.
[51] Int. Cl.[6] .................................................. A61K 31/505
[52] U.S. Cl. ............................................................ 514/259
[58] Field of Search ............................................ 514/259

[56] References Cited

U.S. PATENT DOCUMENTS

| | | | |
|---|---|---|---|
| 4,343,804 | 8/1982 | Munson et al. | 424/258 |
| 5,475,105 | 12/1995 | Steiner et al. | 544/48 |
| 5,480,883 | 1/1996 | Spada et al. | 514/249 |
| 5,580,870 | 12/1996 | Barker et al. | 514/234.5 |

FOREIGN PATENT DOCUMENTS

| | | |
|---|---|---|
| 2148324 | 11/1995 | Canada . |
| 0520722 | 6/1992 | European Pat. Off. . |
| 0566226 | 1/1993 | European Pat. Off. . |
| 0602851 | 9/1993 | European Pat. Off. . |
| 0635498 | 7/1994 | European Pat. Off. . |
| 0635498 | 1/1995 | European Pat. Off. . |
| 9515758 | 6/1995 | WIPO . |
| 9519774 | 7/1995 | WIPO . |
| 9519970 | 7/1995 | WIPO . |
| 9521613 | 8/1995 | WIPO . |
| 9523141 | 8/1995 | WIPO . |
| 9524190 | 9/1995 | WIPO . |
| 9609294 | 3/1996 | WIPO . |
| 9615118 | 5/1996 | WIPO . |
| 9738983 | 10/1997 | WIPO . |

OTHER PUBLICATIONS

Avner, E.D. et al., J. Amer. Soc. Nephrology, 6(3), 1995, p. 690.
Wilson, P.D. et al., Eur. J. Cell. Biol., 61(1), Jun. 1993, pp. 131–138.
Wilson, P.D., Am. J. Kidney Dis., 17(6), Jun. 1991, pp. 634–637.
Fry, D. W. et al., Science, 265:1093–1095 (1994).
Ife, R. J. et al., J. Med. Chem. 35:3413–3422 (1992).
Maguire, M. P. et al., J. Med. Chem. 37:2129–2137 (1994).
Marecki, P. E. et al., Journal of Pharmaceutical Sciences 73:1141–1143 (1984).
Rewcastle, G. W. et al., J. Med. Chem. 38:3482–3487 (1995).
Sarges, R. et al., J. Med. Chem. 36:2828–2830 (1993).

*Primary Examiner*—Kimberly Jordan
*Attorney, Agent, or Firm*—Arnold S. Milowsky

[57] ABSTRACT

This invention provides a method of treating or inhibiting polycystic kidney disease in a mammal in need thereof which comprises administering to said mammal a compound having the formula

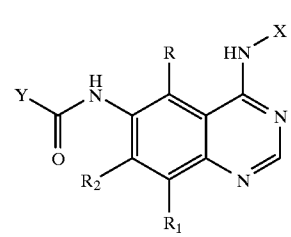

wherein:
  X is phenyl which is optionally substituted;
  R and $R_1$ are each, independently, hydrogen, halogen, alkyl, alkoxy, hydroxy, or trifluoromethyl;
  $R_2$ is hydrogen, alkyl, alkoxy, hydroxy, trifluoromethyl;
  Y is a radical selected from the group consisting of

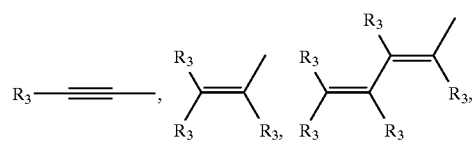

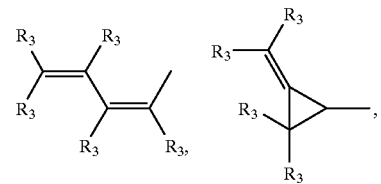

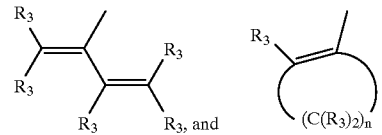

$R_3$ is independently hydrogen, alkyl, carboxy, carboalkoxy, phenyl, or carboalkyl; n=2–4;
or a pharmaceutically acceptable salt thereof, with the proviso that each $R_3$ of Y may be the same or different.

14 Claims, No Drawings

METHOD OF TREATING POLYCYSTIC KIDNEY DISEASE

This application claims the benefit of U.S. Provisional Application No. 60/045,679, filed May 6, 1997.

BACKGROUND OF THE INVENTION

This invention relates to the use of certain quinazoline compounds in the treatment of polycystic kidney disease.

Polycystic Kidney Disease occurs in two forms; autosomal recessive (ARPKD) and autosomal dominant (ADPKD). The two forms of the disease have distinct genetic bases and two genes causing ADPKD have been identified while those of ARPKD have not. The manifestations of the disease are however very similar. Both result from a hyperproliferation of tubule epithelial cells that ultimately results in destruction of tubular structure with cyst formation leading to chronic renal failure. The reason for cyst formation is becoming more clear, in that, there is good evidence that the level of growth factors EGF/TGFα (these two growth factors share the same cellular receptor) are greatly increased in the cyst fluid in these lesions. In addition, it has been noted both the ARPKD and ADPKD that the EGF receptor is mislocated, being present on the luminal surface near the cyst fluid as opposed to the basolateral region as in normal tubular epithelial cells. It has also been shown that TGFα and EGF induce cysts in renal tissues in vitro. In addition, TGFα overexpression in transgenic mice is cystogenic in vivo, that is, animals that have a constitutive overexpression of TGFα will develop kidney cysts. Furthermore, renal cyst fluid contains EGR and EGF like peptides in mitogenic concentrations and finally cystic renal tissue has increased TGFα expression.

DESCRIPTION OF THE INVENTION

This invention provides a method of treating or inhibiting polycystic kidney disease in a mammal in need thereof which comprises administering to said mammal a compound of formula 1:

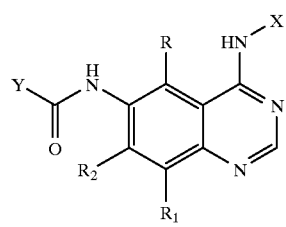

wherein:
X is phenyl optionally substituted with one or more substituents selected from the group consisting of halogen, alkyl of 1–6 carbon atoms, alkoxy of 1–6 carbon atoms, hydroxy, trifluoromethyl, cyano, nitro, carboxy, carboalkoxy of 2–7 carbon atoms, carboalkyl of 2–7 carbon atoms, amino, and alkanoylamino of 1–6 carbon atoms;

R and $R_1$ are each, independently, hydrogen, halogen, alkyl of 1–6 carbon atoms, alkoxy of 1–6 carbon atoms, hydroxy, or trifluoromethyl;

$R_2$ is hydrogen, alkyl of 1–6 carbon atoms, alkoxy of 1–6 carbon atoms, hydroxy, trifluoromethyl;

Y is a radical selected from the group consisting of

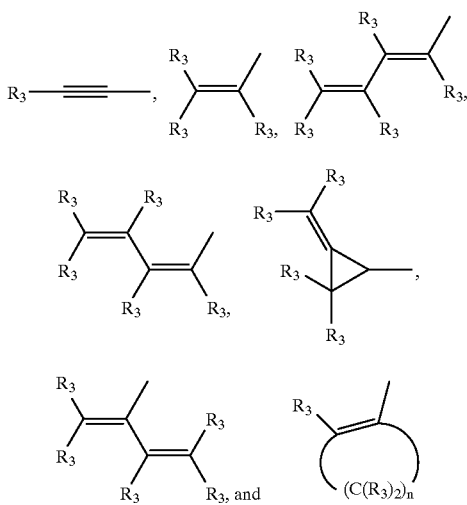

$R_3$ is independently hydrogen, alkyl of 1–6 carbon atoms, carboxy, carboalkoxy of 1–6 carbon atoms, phenyl, or carboalkyl of 2–7 carbon atoms;

n=2–4;

or a pharmaceutically acceptable salt thereof, with the proviso that each $R_3$ of Y may be the same or different.

The pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

The alkyl portion of the alkyl, alkoxy, carboalkoxy, carboalkyl, and alkanoylamino substituents include both straight chain as well as branched carbon chains. Carboxy is defined as a —$CO_2H$ radical. Carboalkoxy of 2–7 carbon atoms is defined as a —$CO_2R"$ radical, where R" is an alkyl radical of 1–6 carbon atoms. Carboalkyl is defined as a —COR" radical, where R" is an alkyl radical of 1–6 carbon atoms. When X is substituted, it is preferred that it is mono-, di-, or tri-substituted, with monosubstituted being most preferred. When a compound of this invention contains an asymmetric center, this invention covers the individual R and S entantiomers as well as the racemate with respect to such compound.

Of the compounds of this invention, preferred members include those in which R, $R^1$, and $R^2$ are hydrogen; and those in which R, $R^1$, and $R^2$ are hydrogen and X is either unsubstituted or monosubstituted with halogen or alkyl of 1–6 carbon atoms.

The preparation of the compounds of this invention encompassed by Formula 9 is described below in Flowsheet A where R, $R_1$, $R_2$, $R_3$, X, and n are defined and R4 is alkyl of 1–6 carbon atoms (preferably isobutyl). Y' is a radical selected from the group consisting of:

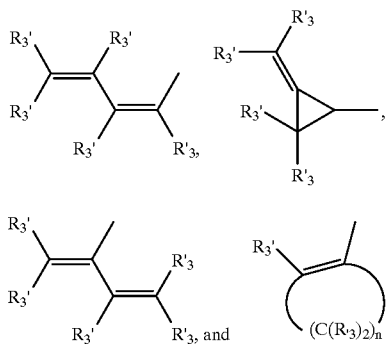

wherein each $R'_3$ is independently alkyl of 1–6 carbon atoms, carboxy, carboalkoxy of 1–6 carbon atoms, phenyl, or carboalkyl of 2–7 carbon atoms. According to the sequence of reaction outlined in flowsheet A, a 5-nitro-anthranilonitrile of Formula 2 is heated at about 100° C. with or without solvent containing an excess of dimethylformamide dimethyl acetal to furnish an amidine of Formula 3. Heating a solution of amidine 3 and the aniline 4 in acetic acid for 1 to 5 hours gives the 6-nitro-4-anilinoquinazolines of Formula 5. Reduction of the nitro group of 5 using a reducing agent such as iron in an acetic acid-alcohol mixture at elevated temperature gives the 6-amino-4-anilinoquinazolines of Formula 6. Acylation of 6 with either an acid chloride of Formula 7 or a mixed anhydride of Formula 8 (which is prepared from the corresponding carboxylic acid) in an inert solvent such as tetrahydrofuran (THF) in the presence of an organic base such as pyridine or triethylamine gives the compounds of this invention represented by Formula 9. In those cases where 7 or 8 have an asymmetric carbon atom, they can be used as the racemate or as the individual R or S entantiomers in which case the compounds of this invention will be in the racemic or R and S optically active forms, respectively. The 5-nitro-anthranilonitriles of Formula 2 needed to prepare the compounds of this invention are either already known to the art or can be prepared by procedures known in the art as detailed in the following references: Baudet, Recl.Trav.Chim.Pays-Bas, 43, 710 (1924); Hartmans, Recl.Trav.Chim.Pays-Bas, 65, 468, 469 (1946); Taylor et al., J.Amer.Chem.Soc., 82, 6058,6063 (1960); Taylor et al., J.Amer.Chem.Soc., 82, 3152,3154 (1960); Deshpande; Seshadri, Indian J.Chem., 11, 538 (1973); Katritzky, Alan R.; Laurenzo, Kathleen S., J.Org.Chem., 51 (1986); Niclas, Hans-Joachim; Bohle, Matthias; Rick, Jens-Detlev; Zeuner, Frank; Zoelch, Lothar, Z.Chem., 25(4), 137–138 (1985).

FLOWSHEET A

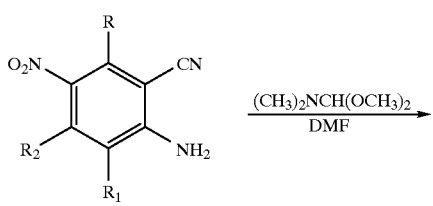

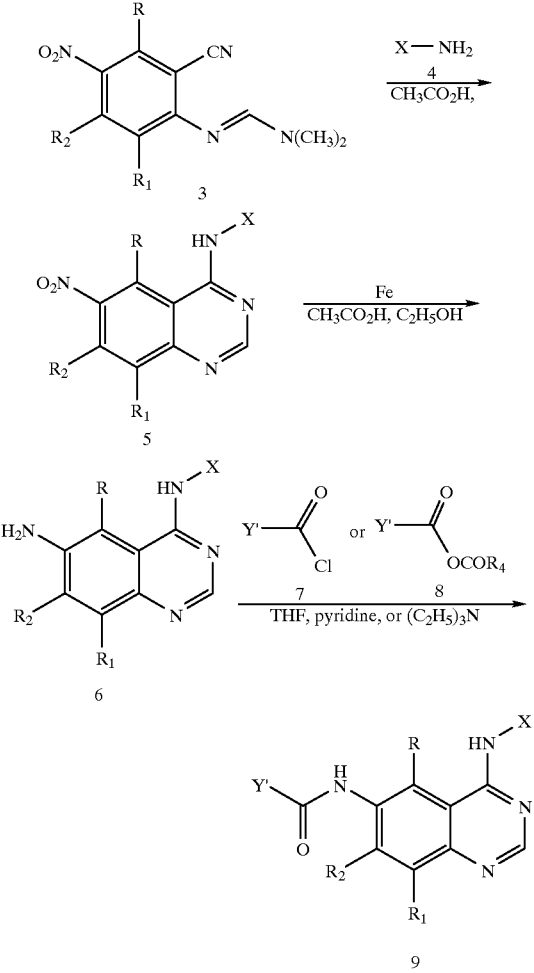

The preparation of the compounds of this invention encompassed by Formula 12 is described below in Flowsheet B wherein R, $R_1$, $R_2$, X, and n are described above. Each $R_5$ is independently hydrogen, phenyl, or alkyl of 1–6 carbon atoms. According to the reaction outlined in Flowsheet B, the 6-amino-4-anilinoquinazolines of Formula 10 (prepared as in Flowsheet A) are acylated with a cyclic anhydride of Formula 11 in an inert solvent such as tetrahydrofuran in the presence of a basic catalyst such as pyridine or triethylamine.

FLOWSHEET B

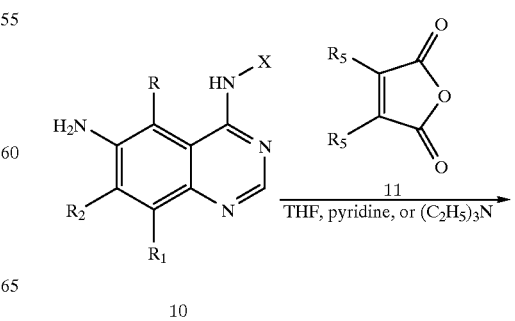

-continued

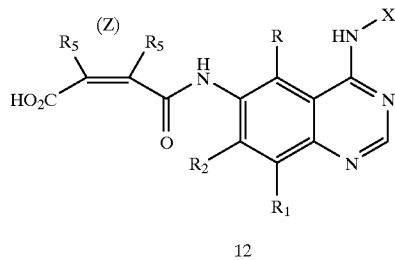

12

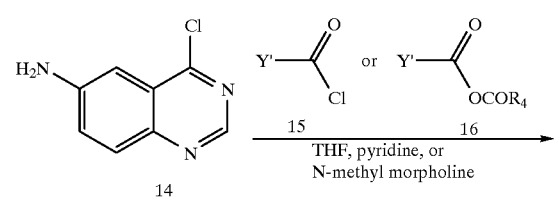

Representative compounds of this invention were evaluated in several standard pharmacological test procedures that showed that the compounds of this invention possess significant activity as inhibitors of protein tyrosine kinases, and are antiproliferative agents. Based on the activity shown in the standard pharmacological test procedures, the compounds of this invention are therefore useful as antineoplastic agents. The test procedures used and results obtained are shown below.

The preparation of the compounds of this invention encompassed by Formula 19 is described below in Flowsheet C wherein Y', $R_4$, and X are described above. According to the reactions outlined in Flowsheet C, 4-choro-6-nitroquinazoline, 13, (Morley, J S. and Simpson, *J. Chem. Soc.*, 360 (1948)) is reduced to 6-amino-4-chloroquinazoline, 14, using a reducing agent such as sodium hydrosulfite in a two phase system consisting of tetrahydrofuran and water in the presence of a small amount of phase transfer catalyst. Acylation of 14 with either an acid chloride of Formula 15 or a mixed anhydride of Formula 16 (which is prepared from the corresponding carboxylic acid) in an inert solvent such as tetrahydrofuran (THF) in the presence of an organic base such as pyridine or N-methyl morpholine gives the compounds of Formula 17. In those cases where 15 or 16 have an asymmetric carbon atom, they can be used as the racemate or as the individual R or S entantiomers in which case the compounds of this invention will be in the racemic or R and S optically active forms, respectively. Heating a compound of Formula 17 with an aniline of Formula 18, in a inert solvent such as isopropanol, gives the compounds of this invention represented by Formula 19.

FLOWSHEET C

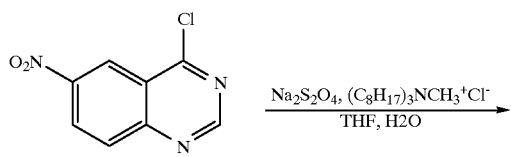

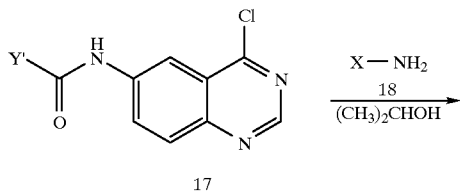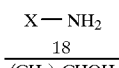

The preparation of the compounds of this invention encompassed by Formula 26 is described below in Flowsheet D wherein Y', $R_4$, and X are described above. According to the reactions outlined in Flowsheet D, the nitro group of 20 (prepared as in Flowsheet A) is reduced to the corresponding amino compound 21 using a palladium catalyst and a source of hydrogen which can be hydrogen itself or cyclohexene. Acylation of 21 with either an acid chloride of Formula 22 or a mixed anhydride of Formula 23 (which is prepared from the corresponding carboxylic acid) in an inert solvent such as tetrahydrofuran (THF) in the presence of an organic base such as pyridine or N-methyl morpholine gives the compounds of Formula 24. In those cases where 22 or 23 have an asymmetric carbon atom, they can be used as the racemate or as the individual R or S entantiomers in which case the compounds of this invention will be in the racemic or R and S optically active forms, respectively. Heating a compound of Formula 24 with an aniline of Formula 25, in a inert solvent such as acetic acid gives the compounds of this invention represented by Formula 26.

FLOWSHEET D

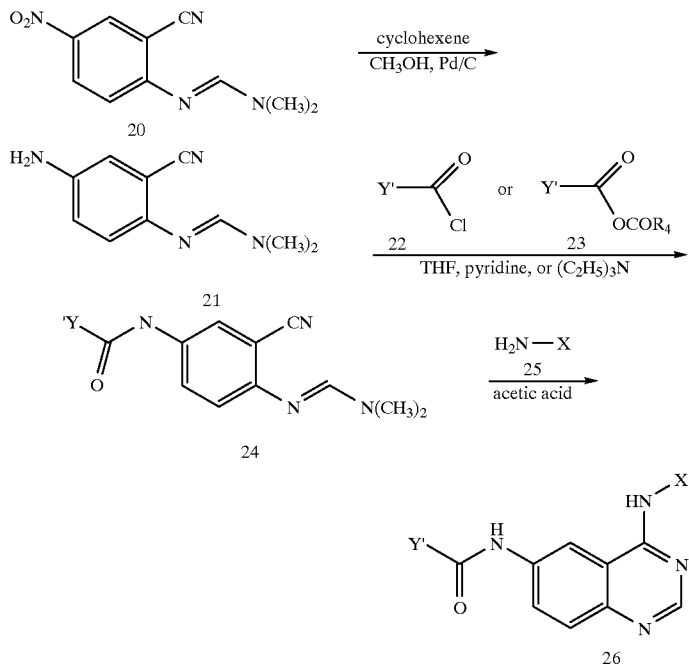

The ability of the compounds of this invention to treat or inhibit polycystic kidney disease was demonstrated in in vitro and in vivo standard pharmacological test procedures as described below. The compound of Example 9 was evaluated in these procedures, which emulate polycystic kidney disease in humans, as a representative compound of this invention.

In Vitro Evaluation: Metanephric Organ Culture

This in vitro standard pharmacological test procedure measured the ability of the test compound to inhibit EGF receptor binding (western analysis of immunoprecipitated activated RGF-R) and to inhibit the formation of tubular cysts (cystic index) in fetal mouse metanephros cell culture. The procedure using serum-free culture of fetal mouse metanephros has been previously described in detail [Avner, E. D., Pediatr. Nephrol. 2: 92 (1989); Avner, E. D., Kidney Int. 36: 960 (1989); Pediatr. nephrol. 4: 372 (1990); Sweeney, W. E., J. Tiss. Cult. Meth. 13: 163 (1991); Pugh, J. P., Kidney Int. 47: 774 (1995)]. Briefly, intact methanephrae from Swiss Webster albino mouse embryos (E13±0.4 days gestation) or whole kidneys from day E-15 through P-14 are cut into 150 um slices, were cultured in chemically defined medium for 120 hours in a Trowell-type organ culture assembly at 36±0.5° C. and 95% humidity in a mixed air—5% $CO_2$ environment. The basal medium consisted of equal volumes of Dublecco's modified Eagle's medium and Ham's F-12 medium supplemented with insulin ($8.3×10^{-7}$M), prostaglandin $E_1$($7.1×10^{-8}$M), selenium $6.8×10^{-9}$M)), transferrin ($6.2×10^{-8}$M) and triiodothyronine ($2×10^{-9}$M).

Supplemented medium consisted of the basal medium to which either EGF (15 ng/ml) or EGF (15 ng/ml) plus the compound of Example 9 at concentrations of 0.1 nM and 1 nM (solublized in DMSO). Day 14 cystic (BPK) and control (Balb/C) explants were cultured for 120 hours under the following conditions:
1. Basal medium to which DMSO was added as a control for drug solvent
2. EGF (15 ng/ml)
3. EGF (15 ng/ml) for 120 hours and Example 9 (0.1 nM) for 2 hours daily
4. EGF (15 ng/ml) and Example 9 (0.1 nM) for 120 hours
5. EGF (15 ng/ml) and Example 9 (1.0 nM) for 120 hours In each culture, tissue culture medium was replaced with freshly prepared medium every 24 hours.

Explant cultures were harvested at 120 hrs., homogenized and the cells disrupted by passage through a 21 gauge needle. [Donaldson, R. W., Proc. Natl. Acad. Sci. USA 89: 8477 (1992); Honegger, A. M., J. Cell Biol. 110: 1541 (1990]. The cellular debris was pelleted and the supernatant transferred to a microfuge tube to which was added 4.0 ug of anti-EGFR per ug of total protein. The mixture was incubated for one hour and 50 ul of protein A/G PLUS-Agarose was added and this mixture was incubated at 4° C. for a further 12 hours. The tubes were centrifuged for 20 minutes at 4° C. to collect the immunoprecipitates. The supernatant was discarded and the pellet was washed twice with 1 ml of RIPA buffer containing protease inhibitors. After a final wash the pellet was resuspended in 25 ul of RIPA to which was added 5×Lanelli's sample buffer. The mixture was boiled for 5 min and then analyzed using a western analysis format with anti-phosphotyrosine antibodies. The results in this test procedure showed that phosphorylation of the EGF receptor occurred in the presence of EGF, and was inhibited by the compound of Example 9, under all three protocols, with 1.0 nM showing the greatest inhibition. These findings are consistent with an inhibition of receptor function.

The degree of proximal tubular cyst formation was quantitated by utilization of a cystic index. The index has been derived from basic light morphometric methods [Loud, A. V., Lab Invest. 50: 250 (1984)] and has been standardized as a tool for quantitation of cyst formation in organ culture systems [Pugh, J. P., Kidney Int. 47: 774 (1995); Avner, E.

D., Kidney Int. 28: 447 (1985); Avner E. D., J. Lab. Clin. Med. 109: 441 (1987)]. Following routine histologic preparation, 8 to 10 serial 3 $\mu$M sections of intact explants were graded, with an eyepiece micrometer, for cyst formation in *Lotus tetragonolobus*—positive tubular segments and *Dolichos biflorus*—positive tubular segments on a scale of 0 (no observable cysts) through 5 (multiple cysts larger than 0.20 mm). For each treatment group, a cystic index was determined on a total of 6 to 8 explants following 120 hours of incubation according to the following scale.

| Cystic index | |
|---|---|
| 0 - no cyst observed | |
| 1 - single or multiple cysts | 0.05 mm |
| 2 - multiple cysts | >0.05 mm; ≦0.10 mm |
| 3 - multiple cysts | >0.10 mm; ≦0.15 mm |
| 4 - multiple cysts | >0.15 mm; ≦0.20 mm |
| 5 - multiple cysts | >0.20 mm |

The following table summarizes the results which were obtained.

| Treatment Group | Cystic Index |
|---|---|
| Basal Media | 3.875 ± 0.25 |
| EGF (15 ng/ml) | 3.5 ± 0.29 |
| EGF (15 ng/ml; 120 h) + Exainple 9 (0.1 nM; 2 hours daily) | 3.375 ± 0.48 |
| EGF (15 ng/ml; 120 h) + Example 9 (0.1 nM; 120 hours) | 1.5 ± 0.5 |
| EGF (15 ng/ml; 120 h) + Example 9 (1.0 nM; 120 hours daily) | 0.75 ± 0.95 |

These results show that the compound of Example 9 reduced collecting tubule cyst lesions in a dose dependent manner, demonstrating the inhibition of cyst formation that is associated with polycystic kidney disease.

Following 120 hours of incubation, intact explants from control and treatment groups were assessed histologically. Tissue was fixed in 4.0% paraformaldehyde in phosphate buffer (pH 7.4) for 30 minutes at 4° C. Explants were then washed, dehydrated through graded acetone, and embedded in plastic embedding medium. Sections were cut at 3 $\mu$M on an ultramicrotome, mounted on glass slides, and stained with hematoxylin or segment specific lectins. Glomeruli were identified histologically as previously described [Sweeney W. E., J. Tiss. Cult. Meth. 13: 163 (1991)]. Proximal tubules were identified by staining with the lectin *Lotus tetragonolobus* (LTA) and collecting tubules were identified by staining with the lectin *Dolichos biflorus* (DBA) [Pugh J. P., Kidney. Int. 47: 774 (1995); Nauta, J., Pediatr. Nephrol. 7: 163 (1993)]. These studies demonstrated that the presence of EGF(15 ng/ml) in the media maintains the cystic structure of the metanephroe. These cysts are stained with DBA—indicating their collecting tubule origin. Identical metanephrae grown in the presence of 15 ng/ml EGF plus 1.0 nM of the compound of Example 9 show a striking regression of collecting tubule cysts with little if any toxicity seen in the surrounding parenchyma.

In Vivo Evaluation

Mice were divided into four groups; the first group were BPK (murine model of autosomal recessive PKD) animals treated with 0.25 mg of the compound of Example 9 on days 7, 14, and 21 (given IP); the second group consisted of untreated BPK controls; the third group were treated normal controls (same dosage regimen as above); and the fourth group was untreated normal controls. The untreated BPK litter had 2 visibly cystic pups by day 17. Tissue was harvested from both groups on day 24. Kidneys and livers harvested from both litters were fixed for 30 min in fresh 4% paraformaldehyde, rinsed, and dehydrated with graded acetone. The tissues were left in immunobed for 40 hours, and then were embedded.

Gross analysis of fresh kidneys from the treated BPK group revealed 3 of 8 animals with cystic kidneys, that were only obvious after the animal was opened. The size of the kidneys were larger than the kidneys from the other treated animals, but were much smaller than the untreated cystic kidneys (approximately 40% of untreated cystic kidneys). Treated control kidneys were slightly smaller than untreated control kidneys.

Total kidney volume was evaluated in all four groups. Kidneys from the untreated BPK group were approximately 6 times the size of kidneys from the untreated control group. Kidneys from the treated BPK group were approximately 2 times the size of the kidneys from the untreated BPK group, and were 3 times smaller than kidneys from the untreated BPK group. The kidneys of the treated control group had a slight decrease in kidney volume compared with the kidneys of the untreated control group, without any apparent morphological changes. No nephrotoxicity was observed in the normal mice treated with the compound of Example 9.

Histologic evaluation of control (non-cystic) kidneys revealed a normal morphologic appearance in both treated (compound of Example 9) and untreated groups. Trichrome stains (for fibrosis) of these non-cystic kidneys revealed no fibrotic changes (collagen deposition) in either the treated or untreated kidneys.

Histologic sections of the day 24 untreated cystic kidneys revealed severe cystic disease with small islands of normal renal structures being compressed by expanding cystic lesions. Staining with DBA and LTA showed that at this late stage of cystogenesis the lesions are almost entirely of collecting tubule origin. It is noteworthy that collecting tubule origin of cystic lesions is characteristic of human ARPKD.

In contrast to these untreated kidneys, kidneys derived from animals treated with three weekly injections of the compound of Example 9 (30 mg/kg) showed only mild to moderate cystic disease with clearly demonstrable normal collecting tubules amongst residual small proximal tubule cysts. In addition, trichrome staining (for fibrosis) of kidneys from the group treated with the compound of Example 9 showed a considerable reduction in collagen deposition and a well organized array of tubular structures.

Histologic staining of the liver revealed a normal portal triad in control untreated animals. In contrast, livers from BPK animals were abnormal with multiple bile ducts and marked biliary epithelial hyperplasia. The livers from BPK animals that were treated with the compound of Example 9 showed a dramatic improvement in morphology with only slight biliary hyperplasia. This effect of the compound of Example 9 in the liver is the first demonstration of the potential reversibility of liver disease in this murine standard pharmacological test procedure 1of PKD.

Based on the results obtained for representative compounds of this invention, the compounds of this invention are useful in treating or inhibiting polycystic kidney disease.

The compounds of this invention may formulated neat or may be combined with one or more pharmaceutically acceptable carriers for administration. For example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solution or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 1000 mg/kg of animal body weight, optionally given in divided doses two to four times a day, or in sustained release form. For most large mammals the total daily dosage is from about 1 to 1000 mg, preferably from about 2 to 500 mg. Dosage forms suitable for internal use comprise from about 0.5 to 1000 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

In some cases it may be desirable to administer the compounds directly to the airways in the form of an aerosol.

These active compounds may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The preparation of representative examples of the compounds of this invention is described below.

EXAMPLE 1

N'-(2-Cyano-4-nitrophenyl)-N,N-dimethylformamidine

A 40.8 g portion of 5-nitro-anthranilonitrile and 40 ml of N,N-dimethylformamide dimethyl acetal were heated on a steam bath for 2 hours. The solvents were removed at reduced pressure and the residue was taken up in methylene chloride. After passing this solution through Magnesol the solvent was removed. After washing with ether 50.8 g of N'-(2-cyano-4-nitrophenyl)-N,N-dimethylformamidine was obtained.

EXAMPLE 2

N-(3-Bromophenyl)-6-nitro-4-quinazolinamine

A solution of 23.74 ml of 3-bromo aniline and 40.5 g N'-(2-cyano-4-nitrophenyl)-N,N-dimethylformamidine in 100 ml of glacial acetic acid was stirred and heated in an oil bath at 148° C. for 1.5 hours. On cooling, filtration of the resulting solid gives a quantitative yield of N-(3-bromophenyl)-6-nitro-4-quinazolinamine: mp=267–270° C.; mass spectrum (m/e): 345.

EXAMPLE 3

N-(3-Bromophenyl)-4,6-quinazolindiamine

A mixture of 34.5 g of N-(3-bromophenyl)-6-nitro-4-quinazolinamine and 16.8 g of iron powder in 150 ml of ethanol and 150 ml of glacial acetic acid was heated in an oil bath at 120° C. for 2 hours. After filtration of the solid, solid sodium carbonate was added to the filtrate giving a solid. This was filtered, and the solid was extracted with methanol. The extracts were treated with charcoal and evaporated to a solid. After washing the solid with ether 27.5 g of N-(3-bromophenyl)-4,6-quinazolindiamine was obtained: mass spectrum (m/e): 315.

EXAMPLE 4

4-[[4-[(3-Bromophenyl)amino]-6-quinazolinyl] amino]-4-oxo-(Z)-2-butenoic acid

A 15 ml portion of pyridine was added to 1.6 g of N-(3-bromophenyl)-4,6-quinazolindiamine and 0.6 g of maleic anhydride. After stirring overnight, the solvents were removed on the rotary evaporator. The solid was taken up in about 400 ml of hot ethanol and the insoluble material filtered to give 0.33 g of 4-[[4-[(3-Bromophenyl)amino]-6-quinazolinyl]amino]-4-oxo-(Z)-2-butenoic acid: mass spectrum (m/e): M+H 413, 415.

EXAMPLE 5

4-[[4[(3-Bromophenyl)amino]-6-quinazolinyl] amino]-4oxo-(E)-2-butenoic acid, ethyl ester A solution of N-(3-bromophenyl)-4,6-quinazolindiamine in 15 ml of pyridine was cooled in an ice bath and a solution of 1.22 g of ethyl fumaryl chloride in 10 ml of methylene chloride was added dropwise. After stirring for 1.5 hours, the reaction was allowed to come to room temperature. The solvents were removed at reduced pressure and the residue was treated with water. The red solid was filtered and extracted into hot acetone. After filtration of the insoluble material, the filtrate was concentrated to give 0.45 g of 4-[[4-[(3-Bromophenyl)amino]-6-quinazolinyl]amino]-4-oxo-(E)-2-butenoic acid, ethyl ester: mp=259–263° C., mass spectrum (m/e): M+H 441, 443.

EXAMPLE 6

N-[4-[(3-Bromophenyl)amino]-6-quinazolinyl]-3-methyl-2-butenamide

A solution of 1.58 g of N-(3-bromophenyl)-4,6-quinazolindiamine in 15 ml of pyridine was cooled in an ice bath and a solution of 0.67 ml of 3,3-dimethylacryloyl chloride in 7 ml of ether was added dropwise. After stirring and cooling for 2 hours, the solvents were removed at reduced pressure. The residue was treated with water and the resulting solid was recrystallized from methyl cellusolve to give 0.97 g of N-[4-[(3-bromophenyl)amino]-6-quinazolinyl]-3-methyl-2-butenamide: mp=300–301° C., mass spectrum (m/e): 396, 398.

EXAMPLE 7

N-[4-[(3-Bromophenyl)amino]-6-quinazolinyl]-(E)-2-butenamide

A solution of 1.6 g of N-(3-bromophenyl)-4,6-quinazolindiamine in 15 ml of pyridine was cooled in an ice bath and a solution of 0.57 ml of trans-crotonoyl chloride in 6 ml of ether was added dropwise. After stirring and cooling for 2 hours, the solvents were removed at reduced pressure. The residue was treated with water and the resulting solid recrystallized from n-butanol to give 0.69 g of N-[4-[(3-bromophenyl)amino]-6-quinazolinyl]-(E)-2-butenamide: mp=153–160° C., mass spectrum (m/e): M+H 383, 385.

EXAMPLE 8

N-[4-[(3-Bromophenyl)amino]-6-quinazolinyl]-2-methyl-2-propenamide

A solution of 1.6 g of N-(3-bromophenyl)-4,6-quinazolindiamine in 15 ml of pyridine was cooled in an ice bath and a solution of 0.59 ml of methacryoyl chloride in 6 ml of ether was added dropwise. After stirring and cooling for 2 hours, the solvents were removed at reduced pressure. The residue was treated with water and the resulting solid was taken up in n-butanol (warming). Addition of ether to the cooled solution gives 0.44 g of N-[4-[(3-bromophenyl)amino]-6-quinazolinyl]-2-methyl-2-propenamide: mp=40–245° C., mass spectrum (m/e): M+H 383, 385.

EXAMPLE 9

N-[4-[(3-Bromophenyl)amino]-6-guinazolinyl]-2-butynamide

A solution of 0.50 g of 2-butynoic acid in 10 ml of tetrahydrofuran was cooled in an ice bath. A 0.79 ml portion of isobutyl chloroformate followed by a 0.66 ml portion of N-methyl morpholine were added. After about 1 minute a solution of 1.6 g of N-(3-bromophenyl)-4,6-quinazolindiamine in 10 ml of pyridine was added. The reaction was allowed to come to room temperature and stir overnight. The solvents were removed at reduced pressure and the solid was recrystallized from n-butanol to give 1.07 g of N-[4-[(3-bromophenyl)amino]-6-quinazolinyl]-2-butynamide: mass spectrum (m/e): 381,383.

EXAMPLE 10

4-[[4-[(3-Bromophenyl)amino]-6-quinazolinyl]amino]-4-oxo-(E)-2-butenoic acid

A 2.5 ml portion of 10 N aqueous sodium hydroxide was added to 2.3 g of 4-[[4-[(3-bromophenyl)amino]-6-quinazolinyl]amino]-4oxo-(E)-2-butenoic acid ethyl ester (Example 5) in 25 ml of ethanol. After stirring for an hour, 2.1 ml of concentrated hydrochloric acid was added, and the reaction was stirred an additional 2 hours. The resulting solid was recrystallized from n-butanol to give 0.97 g of 4-[[4-[(3-Bromophenyl)amino]-6-quinazolinyl]amino]-4-oxo-(E)-2-butenoic acid: mass spectrum (m/e): M+H 413.

EXAMPLE 11

N-[4-[(3-Bromophenyl)amino]-6-quinazolinyl]-2-hexadienamide

A solution of 0.67 g of 2,4-hexadienoic acid in 10 ml of tetrahydrofuran was cooled in an ice bath. A 0.79 ml portion of isobutyl chloroformate followed by a 0.66 ml portion of N-methyl morpholine were added. After about 1 minute a solution of 1.6 g of N-(3-bromophenyl)-4,6-quinazolindiamine in 10 ml of pyridine was added. The reaction was allowed to come to room temperature and stir overnight. The solvents were removed at reduced pressure and the solid was recrystallized to give 1.0 g of N-[4-[(3-bromophenyl)amino]-6-quinazolinyl]-2,4-hexadienamide: mp=258–260° C.

EXAMPLE 12

N-[4-[(3-Bromophenyl)amino]-6-quinazolinyl]-2-cyclopenteneamide

A solution of 0.43 g of 2-cyclopentenoic acid in 5 ml of tetrahydrofuran was cooled in an ice bath. A 0.49 ml portion of isobutyl chloroformate followed by a 0.41 ml portion of N-methyl morpholine were added. After about 1 minute a solution of 1.0 g of N-(3-bromophenyl)-4,6-quinazolindiamine in 10 ml of pyridine was added. The reaction was allowed to come to room temperature and stir overnight. Another 0.5 equivalents of mixed anhydride was added. The mixture was stirred for 5 hours. The solvents were removed at reduced pressure and the solid was purified by chromatography on silica gel to give 0.30 g of N-[4-[(3-bromophenyl)amino]-6-quinazolinyl]-2-cyclopenteneamide: mass spectrum (m/e): 409 (M+H, EI).

EXAMPLE 13

N-[4-[(3-Bromophenyl)amino]-6-quinazolinyl]-2-propenamide

A solution of 2.0 g of N-(3-bromophenyl)-4,6-quinazolindiamine in 10 ml of pyridine was cooled in an ice bath and a solution of 0.61 ml of acryoyl chloride in 30 ml of ether was added dropwise at 0° C. After stirring at room temperature for 3.5 hours, the solvents were removed at reduced pressure. The residue was purified by chromatography to give 0.2 g of N-[4-[(3-bromophenyl)amino]-6-quinazolinyl]-2-propenamide: mass spectrum (m/e): M+H 369.

EXAMPLE 14

N-[4-[(3-Bromophenyl)amino]-6-quinazolinyl]-2-propynamide)

A solution of 0.93 g of 3-phenyl-2-propynoic acid in 10 ml of tetrahydrofuran was cooled in an ice bath. A 0.82 ml portion of isobutyl chloroformate followed by a 0.69 ml portion of N-methyl morpholine were added. After about 1 minute a solution of 1.0 g of N-(3-bromophenyl)-4,6-quinazolindiamine in 7 ml of pyridine was added. The reaction at 0° C. for 1 hr. The solvents were removed at reduced pressure and the solid was purified by chromatography on silica gel to give 0.01 g of N-[4-[(3-bromophenyl) amino]-6-quinazolinyl]-(3-phenyl-2-propynamide): mass spectrum (m/e): 443.2, 445.2 (M+H, electrospray).

EXAMPLE 15

6-amino-4-chlroquinazoline

A mixture consisting of 3.25 g of 4-chloro-6-nitroquinazoline, 10.8 g of sodium hydrosulfite, and 0.3 g of the phase transfer catalyst $(C_8H_{17})_3NCH_3^+$ $Cl^-$ in 97 ml of tetrahydrofuran and 32 ml of water was stirred rapidly for 2 hours. The mixture was diluted with ether and the organic layer was separated. The organic solution was washed with brine and then dried over magnesium sulfate. The solution was passed through a small column of silica gel. The solvent was removed at 30° C. at reduced pressure giving 6-amino-4-chloroquinazoline which is used in the next step without additional purification.

EXAMPLE 16

[4-chloro-6-quinazolinyl]-2-butynamide

A solution of 1.64 g of 2-butynoic acid in 46 ml of tetrahydrofuran was cooled in an ice bath. A 2.34 ml portion of isobutyl chloroformate followed by a 4.13 ml portion of N-methyl morpholine were added. After about 10 minutes, this was poured into a solution of 6-amino-4-chloroquinazoline in 46 ml tetrahydrofuran. This mixture was stirred at room temperature for 2 hours. The mixture was poured into a mixture of brine and saturated sodium bicarbonate and extracted with ether. The ether solution was dried over magnesium sulfate and filtered. The solvent was removed giving [4-chloro-6-quinazolinyl]-2-butynamide as colored oil that was used in the next step without additional purification.

EXAMPLE 17

N-[4-[(3-Bromophenyl)amino]-6-quinazolinyl]-2-butynamide

A solution consisting of 1.76 g of [4-chloro-6-quinazolinyl]-2-butynamide and 1.23 g of 3-bromo aniline was refluxed under an inert atmosphere in 23 ml of isopropanol for 40 minutes. The mixture was cooled to room temperature and 200 ml of ether was added giving 0.4 g of N-[4-[(3-bromophenyl)amino]-6-quinazolinyl]-2-butynamide as the hydrochloride salt. Neutralizing with sodium bicarbonate solution, extracting with ethyl acetate, removal of the solvent, and recyrstallization from 1-butanol gives N-[4-[(3-bromophenyl)amino]-6-quinazolinyl]-2-butynamide as the free base.

EXAMPLE 18

N'-(4-Amino-2-cyanophenyl)-N,N-dimethylformamidine

A solution of 6.0 g (27.5 mmol) of N'-(2-cyano-4-nitrophenyl)-N,N-dimethylformamidine, 33.9 g (41.8 ml, 412.4 mmol) of cyclohexene, and 0.6 g of 10% Pd/C in 360 ml of methanol was refluxed for 4 hrs. The hot mixture was filtered through Celite. Solvent was removed and the residue was recrystallized from chloroform-carbon tetrachloride giving 4.9 g (95%) of the tide compound as a light gray crystalline solid. mass spectrum (m/e): 188.9 (M+H, electrospray).

EXAMPLE 19

N-[3-Cyano-4-[[(dimethylamino)methylene]amino] phenyl]-2-butynamide

To a solution of 2.01 g (23.9 mmol) of 2-butynoic acid and 2.9 ml (22.3 mmol) isobutyl chloroformate in 30 ml tetrahydrofuran was stirred at 0° C. under nitrogen as 2.42 g (2.63 ml, 22.3 mmol) of N-methyl morpholine was added over 3 min. After stirring for 15 min., a solution of N'-(4-amino-2-cyanophenyl)-N,N-dimethylformamidine and 1.6 g (1.75 ml, 15.9 mmol) of N-methyl morpholine in 25 ml tetrahydrofuran was added over 4 min. The mixture was stirred 30 min. at 0° C. and 30 min. at room temperature. The mixture was diluted with 70 ml of ethyl acetate and poured into a mixture of brine and saturated sodium bicarbonate. The organic layer was dried (MgSO$_4$) and filtered through a pad of silica gel. The solvent was removed and the residue was stirred with 50 ml of ether. The suspended solid was collected to give 3.61 g (89%) of an off-white solid. mass spectrum (m/e): 255.0 (M+H, electrospray).

EXAMPLE 20

N-[4-[(3-Bromophenyl)amino]-6-quinazolinyl]-2-butynamide

A solution of 3.0 g (11.8 mmol) of N-[3-cyano-4-[[(dimethylamino)methylene]amino]phenyl]-2-butynamide and 2.23 g (12.98 mmol) of 3-bromo aniline in 18 ml of acetic acid was refluxed gently with stirring under nitrogen for 1 hr 15 min. The mixture was cooled in an ice bath and a solid mass formed. The solid was collected by filtration and washed with ether-acetonitrile 1:1 to give a yellow solid which was recrystallized from ethanol giving 2.51 g of N-[4-[(3-bromophenyl)amino]-6-quinazolinyl]-2-butynamide: mass spectrum (m/e): 381, 383.

We claim:
1. A method of treating or inhibiting polycystic kidney disease in a mammal in need thereof which comprises administering to said mammal a compound of the formula

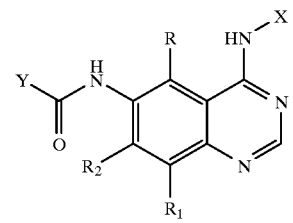

wherein:
X is phenyl optionally substituted with one or more substituents selected from the group consisting of halogen, alkyl of 1–6 carbon atoms, alkoxy of 1–6 carbon atoms, hydroxy, trifluoromethyl, cyano, nitro, carboxy, carboalkoxy of 2–7 carbon atoms, carboalkyl of 2–7 carbon atoms, amino, and alkanoylamino of 1–6 carbon atoms;

R and $R_1$ are each, independently, hydrogen, halogen, alkyl of 1–6 carbon atoms, alkoxy of 1–6 carbon atoms, hydroxy, or trifluoromethyl;

17

R₂ is hydrogen, alkyl of 1–6 carbon atoms, alkoxy of 1–6 carbon atoms, hydroxy, trifluoromethyl;

Y is a radical selected from the group consisting of

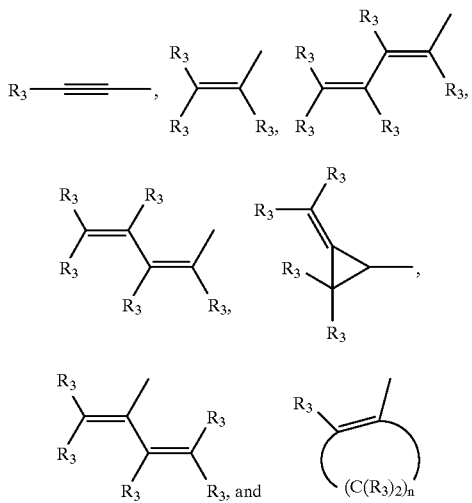

R₃ is independently hydrogen, alkyl of 1–6 carbon atoms, carboxy, carboalkoxy of 1–6 carbon atoms, phenyl, or carboalkyl of 2–7 carbon atoms;

n=2–4;

or a pharmaceutically acceptable salt thereof, with the proviso that each R₃ of Y may be the same or different.

2. The method according to claim 1 wherein R, R₁, and R₂ are hydrogen or a pharmaceutically acceptable salt thereof.

3. The method according to claim 2 wherein X is unsubstituted or substituted with halogen or alkyl of 1–6 carbon atoms.

4. The method according to claim 1 in which N-[4-[(3-Bromophenyl)amino]-6-quinazolinyl]-2-butynamide or a pharmaceutically acceptable salt thereof is administered.

18

5. The method according to claim 1 in which N-[4-[(3-Bromophenyl)amino]-6-quinazolinyl]-2-methyl-2-propenamide or a pharmaceutically acceptable salt thereof is administered.

6. The method according to claim 1 in which N-[4-[(3-Bromophenyl)amino]-6-quinazolinyl]-2,4-hexadienamide or a pharmaceutically acceptable salt thereof is administered.

7. The method according to claim 1 in which N-[4-[(3-Bromophenyl)amino]-6-quinazolinyl]-(E)-2-butenarnide or a pharmaceutically acceptable salt thereof is administered.

8. The method according to claim 1 in which N-[4-[(3-Bromophenyl)amino]-6-quinazolinyl]-3-methyl-2-butenamide or a pharmaceutically acceptable salt thereof is administered.

9. The method according to claim 1 in which 4-[[4-[(3-Bromophenyl)amino]-6-quinazolinyl]amino]-4-oxo-(Z)-2-butenoic acid or a pharmaceutically acceptable salt thereof is administered.

10. The method according to claim 1 in which 4-[[4-[(3-Bromophenyl)amino]-6-quinazolinyl]amino]-4-oxo-(E)-2-butenoic acid or a pharmaceutically acceptable salt thereof is administered.

11. The method according to claim 1 in which 4-[[4-[(3-Bromophenyl)amino]-6-quinazolinyl]amino]-4-oxo-(E)-2-butenoic acid, ethyl ester or a pharmaceutically acceptable salt thereof is administered.

12. The method according to claim 1 in which N-[4-[(3-bromophenyl)amino]-6-quinazolinyl]-2-cyclopentenamide or a pharmaceutically acceptable salt thereof is administered.

13. The method according to claim 1 in which N-[4-[(3-Bromophenyl)amino]-6-quinazolinyl]-2-propenamide or a pharmaceutically acceptable salt thereof is administered.

14. The method according to claim 1 in which N-[4-[(3-bromophenyl)amino]-6-quinazolinyl]-(3-phenyl-2-propynamide) or a pharmaceutically acceptable salt thereof is administered.

* * * * *